(12) United States Patent
Ivachtchenko et al.

(10) Patent No.: US 9,381,201 B2
(45) Date of Patent: Jul. 5, 2016

(54) PHARMACEUTICAL COMPOSITION AND KIT FOR TREATING BACTERIAL INFECTIONS

(71) Applicants: Alexandre Vasilievich Ivachtchenko, Encinitas, CA (US); Andrey Alexandrovich Ivashchenko, Moscow (RU); Nikolay Filippovich Savchuk, Rancho Santa Fe, CA (US)

(72) Inventors: Alexandre Vasilievich Ivachtchenko, Encinitas, CA (US); Sergey Yevgenievich Tkachenko, San Diego, CA (US); Vadim Vasilievich Bichko, San Diego, CA (US)

( * ) Notice: Subject to any disclaimer, the term of this patent is extended or adjusted under 35 U.S.C. 154(b) by 37 days.

(21) Appl. No.: 14/354,141

(22) PCT Filed: Oct. 25, 2012

(86) PCT No.: PCT/RU2012/000871
§ 371 (c)(1),
(2) Date: Apr. 25, 2014

(87) PCT Pub. No.: WO2013/062445
PCT Pub. Date: May 2, 2013

(65) Prior Publication Data
US 2014/0303155 A1    Oct. 9, 2014

(30) Foreign Application Priority Data

Oct. 26, 2011    (RU) ................................ 2011143086

(51) Int. Cl.
| | |
|---|---|
| *A61K 31/5383* | (2006.01) |
| *A61K 31/473* | (2006.01) |
| *A61K 31/4745* | (2006.01) |
| *A61K 31/496* | (2006.01) |
| *A61K 31/395* | (2006.01) |
| *A61K 9/00* | (2006.01) |
| *A61K 45/06* | (2006.01) |
| *A61K 9/20* | (2006.01) |
| *A61K 9/48* | (2006.01) |
| *A61K 31/513* | (2006.01) |

(52) U.S. Cl.
CPC ........... *A61K 31/5383* (2013.01); *A61K 9/0019* (2013.01); *A61K 9/2018* (2013.01); *A61K 9/4858* (2013.01); *A61K 31/395* (2013.01); *A61K 31/473* (2013.01); *A61K 31/4745* (2013.01); *A61K 31/496* (2013.01); *A61K 31/513* (2013.01); *A61K 45/06* (2013.01)

(58) Field of Classification Search
None
See application file for complete search history.

(56) References Cited

U.S. PATENT DOCUMENTS 6,316,433 B1 *    11/2001    Rose ..................... A61K 31/00
514/183

FOREIGN PATENT DOCUMENTS

| RU | 2296996 | * | 4/2007 |
| RU | 2297846 | * | 4/2007 |

OTHER PUBLICATIONS

English translation of RU 2297846 (2007).*
English translation of RU 2296996 (2007).*

* cited by examiner

*Primary Examiner* — Bong-Sook Baek

(57) ABSTRACT

The invention relates to pharmacology and medicine, more particularly to novel pharmaceutical compositions and pharmaceutical kits for treating bacterial infections, and to novel method for treating diseases caused by bacterial infections including tuberculosis. The pharmaceutical composition is disclosed comprising Rifamycin and interferon inducer in pharmacologically effective doses, and also pharmaceutical kit for treating diseases caused by bacterial and healthcare acquired infections, comprising pharmacologically effective doses of Rifamycin in the form of a tablet, a capsule or an injection, interferon inducer in the form of a tablet, a capsule or an injection, and instruction for administration of the components of this pharmaceutical kit.

3 Claims, 1 Drawing Sheet

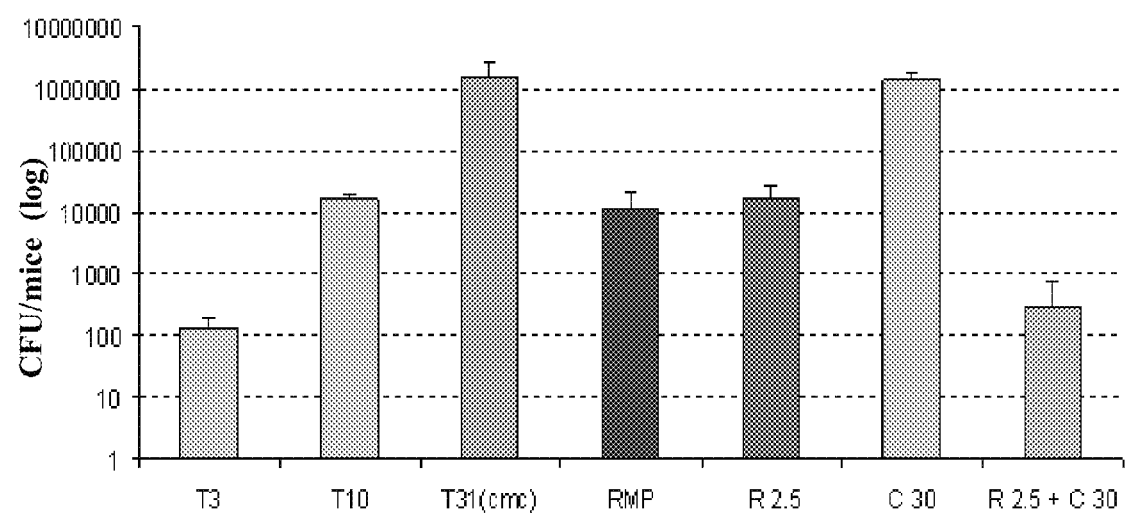

PHARMACEUTICAL COMPOSITION AND KIT FOR TREATING BACTERIAL INFECTIONS

CROSS REFERENCE TO RELATED APPLICATIONS

This application is a National stage of International application PCT/RU2012/000871 filed Oct. 25, 2012, which claims benefit of foreign priority to the Russian Federation application RU 2011143086 of Oct. 26, 2011. The priority applications are hereby incorporated by reference in their entirety.

FIELD OF INVENTION

The invention relates to pharmacology and medicine, more particularly to novel pharmaceutical compositions and pharmaceutical kits for treating bacterial infections, and to novel method for treating diseases caused by bacterial infections including tuberculosis.

PRIOR ART

Until very recently investigation in the field of tuberculosis therapy had the trend of either searching for novel active compounds and their combinations with conventional medicaments (WO 1995/13807, publ. May 26, 1995; EP 0650728A1, publ. May 3, 1995; EP 0398165A1, publ. Nov. 22, 1990; U.S. Pat. No. 5,399,558, publ. Mar. 21, 1995), or creation of novel pharmaceutical formulations for such well-known drug substances as Isoniaside, Rifampicin, Ethambutol (WO88/006038, publ. Aug. 25, 1988; U.S. Pat. No. 5,811,088, publ. Sep. 22, 1998; RU 2143900C1, publ. Jan. 10, 2000; RU 2087146C1, publ. Aug. 20, 1997; RU2125451C1, publ. Jan. 27, 1999).

A group of effective antibiotics Rifamycins exhibiting antibacterial action of wide range [Rifapentine (U.S. Pat. No. 4,002,752), Rifaximin (U.S. Pat. No. 4,341,785), Rifabutin (GB1603127), Rifampicine and Rifalazil]—belonging to the class of Ansamycins which are formed in biosynthesis by one of Actinomycetes, as well as their semi-synthetic derivatives are well known. Among them Rifampicin and Rifalazil—semi-synthetic derivatives of Rifamycin SV—exhibit the widest range of antimicrobial action and good drug absorbability.

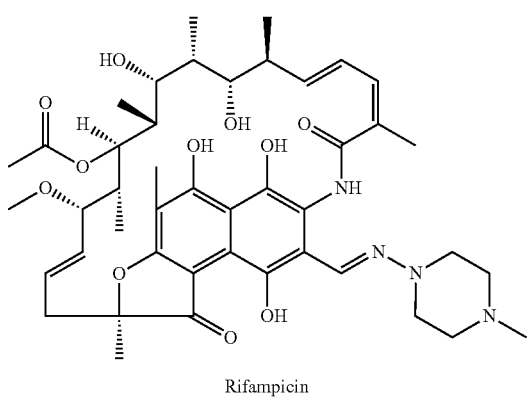

Rifampicin

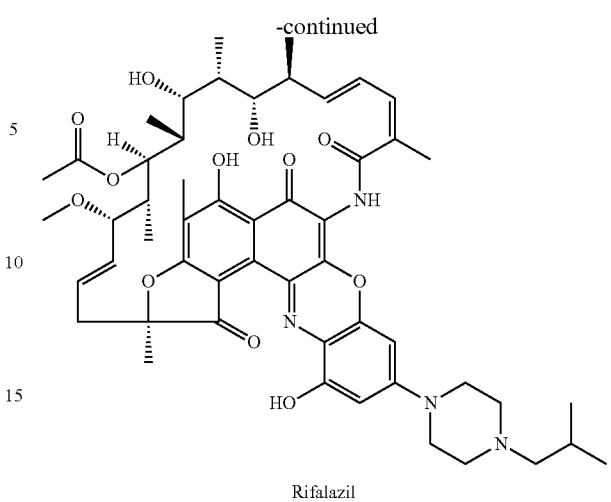

Rifalazil

Many gram-positive microorganisms (minimal inhibiting concentration 0.001-0.1 µg/ml) and a large number of gram-negative bacteria (minimal inhibiting concentration 1-10 µg/ml) are sensitive to Rifampicin. At low concentrations Rifampicin is active towards *Mycobacterium tuberculosis, Mycobacterium avium complex, Chlamydia pneumoniae, Chlamydia trachomatis, Helicobacter pylory, Clostridium difficile, Bructlla* spp., *Legionella pntumophila, Rickettsia typhi, Mycobacterium leprae, Staphylococcus aureus,* including methicillin-resistant strains, *Staphylococcus epidermidis*; streptococci; at high concentrations—towards some gram-negative microorganisms (*Escherichia coli, Klebsiella, Proteus, Neisseria meningitides, Neisseria gonorrhoeae,* among them beta-lactam forming) It is active towards *Haemophilus influenza* (including those resistant to Ampicillin and Chloramphenicol), *Haemophilus ducreyi,* and other gram-positive anaerobes. The unique property of Rifampicin is its high activity against tuberculosis *Mycobacterium* (minimal inhibiting concentration 0.005-0.5 µg/ml), that accounts for the leading position of this antibiotic in the commonly used schemes of treating tuberculosis. Rifampicin is highly active against gram-positive cocci, among them multi resistant cocci and so named methicillin-resistant cocci. Over 95% of *Streptococcus pyogenes* which are resistant to penicillin and other antibiotics, as well as pneumococci, are sensitive to Rifampicin. *Bacillus antrhracis* and pathogenic Clostridia are highly sensitive to Rifampicin. It is active against many strains of bacteroides, Proteus, Providencias, causative agents of *Legionella* diseases and brucellosis. Rifampicin is one of the most active agents in leprosy treatment. It exceeds activity of various tetracyclines towards Chlamydias—*Chlamydia trachomatis*, parrot fever and lymphogranuloma causative agents. Rifampicin is highly effective against Prowazeki *Rickettsia*.

Mechanism of Rifampicins antimicrobial action differs from the mechanism of action of all the other antibiotics. It inhibits RNA synthesis by means of forming a complex with RNA-polymerase which is DNA-dependent. This effect is sufficiently selective. Rifampicin is acting as bactericidal agent on proliferating bacteria, it penetrates into the cells and inhibits pathogens located there. Resistance to Rifampicin is rapidly developing in the course of treatment. In order to overcome this effect Rifampicin is prescribed in combination with other antibiotics.

Synergy was discovered for combined action of Rifampicin and some other antibiotics, such as Erythromycin (towards staphylococci), Tetracycline (towards *Salmonella, Escherichia, Shigela*), and Novobiocin (towards *Salmonella*). Synergistic or additive effect of Rifampicin and Trimethoprim in relation to many microorganisms was also detected. Therefore, fixed doses of combination of Rifampicin and Trimethoprim (Rifaprim agent) are used. In the treatment of tuberculosis Rifampicin is only prescribed together with other antituberculosis agents (Stretomycin, Ethambutol, Isoniazid). Rifampicin is highly effective when taken orally: in some tissues it was found in concentrations exceeding its concentration in blood serum. It penetrates through hematoencephalic barrier, placental barrier, cell membranes; it is removed from organism mainly with the bile.

Rifalazil is also known as KRM-1648 or benzoxazinorifamycin [U.S. Pat. No. 4,690,019 publ. Sep. 1, 1987; U.S. Pat. No. 4,983,602, publ. Jan. 8, 1991; U.S. Pat. No. 6,316,433, Nov. 13, 2001; U.S. Pat. No. 6,566,354, publ. May 20, 2003], exhibits antibacterial activity towards wide range of pathogens (including *Mycobacterium tuberculosis, Mycobacterium avium complex, Chlamydia pneumoniae, Chlamydia trachomatis, Helicobacter pylory Clostridium difficile*, Mycobacteria, methicillin-resistant strains *Staphylococcus aureus* and other gram-positive polyresistant bacteria and healthcare acquired infections), prolonged half-life of elimination (more then 100 h), as well as high penetration into the cells (>300:1). Everything above said reveals higher effectiveness of Rifalazil in comparison with the drugs used in conventional therapy used for a number of diseases, among them tuberculosis and nongonococcal urethritis.

Rifalazil is also used in combination therapy of bacterial infections together with beta-lactam inhibitors, amino glycosides, Tetracyclines, lipopeptides, macrolides, ketolides, lincosamides, streptogramines, sulfanilamides, oxazolidinones, quinolones, ciprofloxacin and the like [US 20110117154, publ. May 19, 2011].

Rifabutin as well as the drugs described above exhibits a wide range of antibacterial action [http://www.rlsnet.ru/mnn_index_id_2345.htm]. It inhibits selectively DNA-dependent RNA polymeraze in sensitive strains. It is highly effective towards extra- and intracellular located *Mycobacterium* spp., including *Mycobacterium tuberculosis*, complex *Mycobacterium avium*-intracellulare, *Mycobacterium fortuitum, Mycobacterium xenopi*. It is more active then Rifampicin towards intracellular *Mycobacterium tuberculosis* (at concentrations 2 times less). For treatment of active tuberculosis it is used in combination with other antituberculous remedies. It has immune stimulative effect.

Rifaximin [http://www.rlsnet.ru/tn_index_id_36028.htm#opisanie-lekarstvennoj-formy] is an antibacterial drug with wide range of action. Irreversibly binds to the beta subunit of the bacterial enzyme, DNA-dependent RNA polymeraze and, therefore, inhibits synthesis of RNA and bacterial proteins. The result of irreversible binding to enzyme is its bactericidal properties towards sensitive bacteria. The drug has a wide range of antimicrobial activity including most of gram-negative and gram-positive, aerobic and anaerobic bacteria causing gastrointestinal infections, among them traveler's diarrhea. It is highly effective towards aerobic *Staphylococcus* spp., *Enterococcus* spp., and anaerobic *Peptostreptococcus* spp. and others. The drug is used for treating gastrointestinal infections caused by bacteria sensitive to Rifaximin, among them acute gastrointestinal infections, traveler's diarrhea, syndrome of intestinal bacterial overgrowth, hepatic encephalopathy, mild diverticular colon disease and chronic inflammatory bowel disease.

World Health Organization (WHO) points out the urgent necessity of novel combined anti-tuberculosis remedies comprising in one tablet a specially chosen set of medicaments with fixed doses of ingredients, providing an optimal therapeutic effect (Consilium Medicum 1999, v. 2, p. 170-171. Remedium, 2000, 7, 8).

The authors of the invention have found out unexpectedly, that Rifamycins including Rifampicin and Rifalazil in combination with interferon inducers, by contrast to either one Rifamycin or one interferon inducer, exhibit high synergy—more then by an order of magnitude higher anti-infectious activity.

DISCLOSURE OF THE INVENTION

The subject of the present invention is to provide a pharmaceutical composition for treating a disease caused by a bacterial or healthcare acquired infection sensitive to Rifamycins, comprising a Rifamycin and an interferon inducer in a pharmacologically effective dosage in the form of a tablet, a capsule or an injection placed in a pharmaceutically acceptable package.

The preferred is the use of Rifampicin, Rifalazil, Rifapentine, Rifaximin or Rifabutin acting as Rifamycin and the following medicaments: Cycloferon, Larifan, Amiksin, Hiporhamin, Bropirimin, Imiquimod, Resiquimod or IMO-2125 as interferon inducer.

Interferon inducer Bropirimin was described in patent application WO 2007133800, publ. Nov. 22, 2007; Resiquimod was described in US 20050239733, publ. Oct. 27, 2005; IMO-2125 was described in "IMO-2125, an agonist of TLR9, that induces endogenous IFN-alpha up-regulates broader range of gene expression profiles compared to exogenously added IFN-alpha in human PBMCS". J Hepatol 2010, 52 (Suppl. 1): Abst 692.

The more preferable is the pharmaceutical composition comprising Rifampicin acting as a Rifamycin and Cycloferon as an interferon inducer.

The more preferable is also the pharmaceutical composition comprising Rifalazil acting as a Rifamycin and Cycloferon as an interferon inducer.

According to the invention the pharmaceutical composition is intended for treating diseases caused by *Mycobacterium tuberculosis, Mycobacterium avium complex, Chlamydia pneumoniae, Chlamydia trachomatis* or *Helicobacter pylory*.

A pharmaceutical composition may also include stabilizers, carries, diluents and other additives as auxiliary components, which are commonly used for pharmaceutical form production.

The subject of the present invention is to provide a pharmaceutical kit placed in an acceptable package for treating a disease caused by a bacterial and healthcare acquired infection, sensitive to Rifamycins, comprising a pharmacologically effective dosage of a Rifamycin in the form of a tablet, a capsule or an injection, an interferon inducer in the form of a tablet, a capsule or an injection, and an instruction for administration of the components of this pharmaceutical kit.

The preferred pharmaceutical kit is the pharmaceutical kit, intended for treating a disease caused by *Mycobacterium tuberculosis, Mycobacterium avium complex, Chlamydia pneumoniae, Chlamydia trachomatis* or *Helicobacter pylory*.

For preference, pharmaceutical kit comprises Rifampicin, Rifalazil, Rifapentine, Rifaximin or Rifabutin acting as Rifamycin, and Cycloferon, Larifan, Amiksin, Hiporhamin, Bropirimin, Imiquimod, Resiquimod or IMO-2125 as an interferon inducer.

For more preference, the pharmaceutical kit comprises pharmacologically effective doses of Rifampicin in the form of a tablet, a capsule or an injection, Cycloferon in the form of a tablet, a capsule or an injection, and an instruction for administration of the components of this pharmaceutical kit.

It is also more preferable, the pharmaceutical kit comprises pharmacologically effective doses of Rifalazil in the form of a tablet, a capsule or an injection, Cycloferon in the form of a tablet, a capsule or an injection, and instruction for administration of the components of this pharmaceutical kit.

The subject of the present invention is also to provide a method for treating a disease caused by a bacterial and healthcare acquired infection, sensitive to Rifamycins, comprising administering a pharmacologically effective amount of a novel pharmaceutical composition or an effective amount of a composition of a Rifamycin and an interferon inducer from a novel pharmaceutical kit to a subject in need thereof.

The subject of the present invention is also to provide a method for treating tuberculosis, AIDS complicated with tuberculosis or a disease caused by *Mycobacterium tuberculosis, Mycobacterium avium complex, Chlamydia pneumoniae, Chlamydia trachomatis* or *Helicobacter pylory*.

The invention is illustrated by a drawing.

FIG. 1 is a graphical representation of testing results of anti-tuberculosis activity of the disclosed agents on a model of mice infected with *Mycobacterium tuberculosis* (acute tuberculosis infection).

Symbols on FIG. 1: T3—*mycobacterium* titers on the 3 day (moment of infection); T10—*mycobacterium* titers on the 10 day (beginning of administration); T31—(CMC)-mycobacterium titers in control (CMC) on the 31 day (ending of administration); RMP—Rifampicin; R—Rifalazil; C—Cycloferon, CFU—(colony-forming units)—infectious (colony-forming) units in mouse's lungs.

Below the invention is described by means of specific examples, which illustrate, but not limit, the scope of the invention.

EXAMPLE 1

Pharmaceutical Kit

Pharmaceutical kit includes 7 tablets of Rifampicin containing by 250 mg of active ingredient, 7-16 tablets of Cycloferon, containing by 300 mg of active ingredient and instruction for use.

EXAMPLE 2

Pharmaceutical Kit

Pharmaceutical kit includes 7 tablets of Rifalazil, containing by 25 mg of active ingredient, 7-16 tablets of Cycloferon, containing by 150 mg of active ingredient, and instruction for use.

EXAMPLE 3

Preparation of Pharmaceutical Compositions

For preparation of pharmaceutical composition one of Rifamycins and an interferon inducer are mixed together in the ratio mentioned in the Table.

TABLE

| | a Rifamycin, mg | an Interferon inducer, mg |
|---|---|---|
| 3a | Rifampicin - 150-500 (300)* | Cycloferon - 50-450 (300*) |
| 3b | Rifampicin - 150-500 (300)* | Imiquimod - 50-100 (25*) |
| 3c | Rifalazil - 5-50 (25*) | Cycloferon - 50-450 (150*) |

TABLE-continued

| | a Rifamycin, mg | an Interferon inducer, mg |
|---|---|---|
| 3d | 5-50 (25*) | Amiksin - 100-500 (150*) |
| 3e | 5-50 (25*) | Hiporhamin - 20-200 (100*) |
| 3f | 5-50 (25*) | Bropirimin - 500-3000 (750*) |
| 3g | 5-50 (25*) | Resiquimod - 0.05-5.0 (1*) |
| 3h | 5-50 (25*) | IMO-2125 - 5.0-50 (15*) |
| 3i | 5-50 (25*) | Imiquimod - 50-100 (25*) |
| 3j | 5-50 (25*) | Larifan - 0.05-5.0 (0.1*) |

*Preferable composition

EXAMPLE 4

Preparation of Medicament in the Form of Tablets

Starch (11200 mg), grained lactose (11200 mg), talcum (2800 mg), Rifalazil (1000 mg) and Cycloferon (6000 mg) were mixed together and press into a brick. The prepared brick was crushed to granules and riddled through sieves, gathering granules of 14-16 mesh size. The obtained granules were pelletized into tablets of suitable form of 370 mg by weight each.

EXAMPLE 5

Preparation of Medicament in the Form of Capsules

Rifalazil and Cycloferon were carefully mixed with a powder of lactose in ratio 1:6:4. The prepared powdery mixture was packed by 300 mg into gelatinous capsules of suitable size.

EXAMPLE 6

Preparation of Medicament in the Form of Injections

Rifampicin (0.15 g) and Cycloferon (0.15 g) were dissolved in sterile water for injections (2.5 ml), ampoules with the powder were shaken vigorously until complete dissolution; the prepared solution was mixed with 5% glucose solution (125 ml). It gave injection solution for intravenous administration.

EXAMPLE 7

Testing of anti-tuberculosis activity of the disclosed agents on a model of mice infected with *Mycobacterium tuberculosis* (acute tuberculosis infection).

Female mice of BALB/c line weighing 19-20 g. were infected with *Mycobacterium tuberculosis* Erdman (ATCC 35801 catalog) in the chamber for aerosol infection (GlasCol, Terra Haute, Ind.). *Mycobacterium* suspension (10 ml), containing 5 Mio/ml of infectious (colony-forming) units was placed in the spray tube. In 3, 10 and 31 days after infection, the mice that did not receive the tested agents were subjected to euthanasia by means of asphyxia with carbon dioxide, then both halves of the lungs were removed and homogenized in 3 ml of sterile Hanks solution (Balanced Salt Solution, HBSS) in sterile conditions.

6-Well plates with agar (Middlebrook 7H11) were inoculated with serial 10-fold dilutions of the suspension in Hanks solution. The plates were incubated at 37° C. for 18-21 days, then, titers of infectious (colony-forming) units were determined.

The tested compounds (Rifampicin, Rifalazil, Cycloferon, Rifampicin+Cycloferon, Rifalazil+Cycloferon) were dissolved in 0.5% solution of carboxymethyl cellulose, and mice (8 mice in a dose group) were injected with these solutions intraperitoneally by 200 μl on the 10-14, 17-21 and 24-28 days after infection daily. All the mice injected with the tested compounds or placebo (0.5% solution of carboxymethyl cellulose) were subjected to euthanasia on the 31 day after infection, and titers of infectious units in the lung homogenates were determined.

Euthanasia

Mice were placed in the chamber with carbon dioxide. Assure oneself of all the animals were subjected to euthanasia. Then, the animals were placed in 70% solution of ethyl alcohol for 10 minutes.

Preparation of Lung Tissues 2-3 sterile lab wipes were placed on a surgical table. A mouse was got out of alcohol solution and spread on the table. It was fixed with pins. Then incision along the diaphragm and through ribs was made. The breast was opened, the ribs were fixed on both sides by needles (needles should be changed for each animal to avoid contamination). The lungs were carefully extracted and put in a vial with Hanks solution, which had been placed in the ice. The remaining organs were wrapped in lab wipes and placed in a container for biological waste.

Handling of Lung Tissues

Homogenizer was treated with 70% ethanol solution, sterile saline and wiped with sterile lab wipes. Lung samples were homogenized for 10-20 sec or until small pieces of tissues were not seen. Fore every new sample the homogenizer was treated with 70% ethanol solution, sterile saline and wiped with sterile lab wipes. The homogenate was treated with ultrasound for 15 sec using sonicator. The homogenate (100 μl) was placed in a well of 24-well plate and stirred. Serial 10-fold dilutions were prepared. The dilutions in amount of 100 μl were placed into 6-well plates with agar, uniformly distributed over the surface of agar and dried in the air. The plates with agar were turned over and placed in an incubator at 37° C. Incubation lasted for at least 18 days, after that the colonies of mycobacterium were counted.

Lowering of micobacterium titers in mice lungs after 3 week administration of the agents in comparison with the control (CMC) on the 31 day corresponded to:

Rifalazil, 2.5 mg/kg/day−87 times

Cycloferon, 30 mg/kg/day−1.08 times

Rifalazil, 2.5 mg/kg/day+Cycloferon, 30 mg/kg/day−1222 times.

Rifampicin, 20 mg/kg/day+Cycloferon, 30 mg/kg/day 561 times.

As can be seen from the data given Cycloferon in dose of 30 mg/kg/day is not active, Rifalazil (2.5 mg/kg/day) reduces micobacterium titers in mice lungs in 87 times after 3 week administration of the medicament in comparison with control (CMC) on the 31 day, whereas the combination of Rifalazil (2.5 mg/kg/day) and Cycloferon (30 mg/kg/day) yielded synergism and reduced micobacterium titers in mice lungs in 1222 times after 3 week administration of the composition in comparison with the control (CMC) on the 31 day, so combination of Rifalazil and Cycloferon is 14 times (1222: 87=14,04) more active then Rifalazil alone.

Activity determination of the tested specimen in mice, infected with *Mycobacterium avium complex* (mycobacteriosis) or *Chlamydia pneumonia*, (pneumonia) was carried out as described above. Pharmaceutical compositions Rifalazil+Cycloferon and Rifampicin+Cycloferon displayed synergetic effect.

INDUSTRIAL APPLICABILITY

The invention can be used in medicine and veterinary.

The invention claimed is:

1. A pharmaceutical composition for treatment diseases caused by *Mycobacterium tuberculosis*, comprising Rifalazil and Cycloferon as the interferon inducer in pharmacologically effective doses in the form of tablets, capsules or injections placed in acceptable package.

2. A pharmaceutical kit placed in an acceptable package for treating a disease caused by *Mycobacterium tuberculosis*, comprising a pharmacologically effective dosage of Rifalazil in the form of a tablet, a capsule or an injection, Cycloferon as an interferon inducer in the form of a tablet, a capsule or an injection, and an instruction for simultaneous administration of the components of the pharmaceutical kit.

3. A method for treating a disease caused by *Mycobacterium tuberculosis*, comprising administering an effective amount of a pharmaceutical composition according to claim 1 or an effective amount of components from the kit according to claim 2 to a subject in need thereof.

* * * * *